US011464568B2

(12) United States Patent
Strongosky et al.

(10) Patent No.: US 11,464,568 B2
(45) Date of Patent: Oct. 11, 2022

(54) CUSTOMIZABLE SATURATION BIOPSY

(71) Applicant: BEST MEDICAL INTERNATIONAL, INC., Springfield, VA (US)

(72) Inventors: David Strongosky, Carmichaels, PA (US); Sujat M. Sukthankar, Shrewsbury, MA (US)

(73) Assignee: Best Medical International, Inc., Springfield, VA (US)

( * ) Notice: Subject to any disclaimer, the term of this patent is extended or adjusted under 35 U.S.C. 154(b) by 344 days.

(21) Appl. No.: 15/971,239

(22) Filed: May 4, 2018

(65) Prior Publication Data

US 2018/0325598 A1    Nov. 15, 2018

Related U.S. Application Data

(60) Provisional application No. 62/504,202, filed on May 10, 2017.

(51) Int. Cl.
*A61B 34/10* (2016.01)
*A61B 10/02* (2006.01)
(Continued)

(52) U.S. Cl.
CPC .......... *A61B 34/10* (2016.02); *A61B 10/0233* (2013.01); *A61B 90/37* (2016.02);
(Continued)

(58) Field of Classification Search
None
See application file for complete search history.

(56) References Cited

U.S. PATENT DOCUMENTS 4,798,212 A * 1/1989 Arana ................ A61B 17/3403
600/562
5,810,742 A * 9/1998 Pearlman ............. A61B 5/0536
600/547
(Continued)

FOREIGN PATENT DOCUMENTS

WO     WO 2016059498 A1    4/2016

OTHER PUBLICATIONS

3DBiopsy, The Next Dimension, Our System, 3DBiposy, Inc. 2018, 6 pages.

(Continued)

*Primary Examiner* — Sean P Dougherty
*Assistant Examiner* — Benjamin S Melhus

(57) ABSTRACT

A system and method for customized saturation biopsy is provided that facilitates diagnosis, management and treatment of cancer or other disease in a gland or organ. The system includes a pathology mapping unit that identifies a plurality of regions of a biopsy area. A grid assembly is coupled to the pathology mapping unit, the grid assembly including a grid disposed externally to the biopsy area. A display is coupled to the pathology mapping unit that displays information corresponding to the plurality of regions of the biopsy area, the pathology mapping unit controlling a configuration of the grid and the information corresponding to the plurality of regions. An image probe can be provided that acquires at least one image of the biopsy area, and the display displays the at least one image. An interface can be provided that is coupled to the display and supplies information to the pathology mapping unit.

19 Claims, 6 Drawing Sheets

(51) Int. Cl.
*A61B 90/00* (2016.01)
*G06T 7/00* (2017.01)
*G06T 7/73* (2017.01)

(52) U.S. Cl.
CPC .............. *G06T 7/0012* (2013.01); *G06T 7/73* (2017.01); *A61B 2034/107* (2016.02); *A61B 2090/378* (2016.02); *G06T 2207/10068* (2013.01); *G06T 2207/30081* (2013.01); *G06T 2207/30208* (2013.01)

(56) References Cited

U.S. PATENT DOCUMENTS

| | | | | |
|---|---|---|---|---|
| 6,285,902 B1 * | 9/2001 | Kienzle, III | ............ | A61B 6/12 600/427 |
| 6,752,753 B1 * | 6/2004 | Hoskins | ............ | A61M 37/0069 600/7 |
| 2003/0135115 A1 * | 7/2003 | Burdette | ............ | A61M 37/0069 600/437 |
| 2006/0079771 A1 * | 4/2006 | Nir | ............ | A61B 90/36 600/437 |
| 2007/0043291 A1 | 2/2007 | Fidel et al. | | |
| 2007/0225544 A1 * | 9/2007 | Vance | ............ | A61M 37/0069 600/8 |
| 2009/0118640 A1 * | 5/2009 | Miller | ............ | A61B 90/36 600/567 |
| 2009/0118724 A1 * | 5/2009 | Zvuloni | ............ | A61N 7/02 606/27 |
| 2010/0019918 A1 * | 1/2010 | Avital | ............ | A61B 90/11 340/686.4 |
| 2010/0172559 A1 * | 7/2010 | Kumar | ............ | A61B 10/0241 382/131 |
| 2011/0009748 A1 * | 1/2011 | Greene | ............ | A61B 10/0241 600/439 |
| 2012/0027278 A1 * | 2/2012 | Chaney | ............ | G06T 7/344 382/131 |
| 2013/0034282 A1 * | 2/2013 | Kaufman | ............ | G06T 7/0014 382/128 |
| 2013/0116548 A1 * | 5/2013 | Kumar | ............ | A61B 8/0841 600/424 |
| 2013/0303895 A1 * | 11/2013 | Littrup | ............ | A61B 8/403 600/424 |
| 2013/0310680 A1 | 11/2013 | Werahera et al. | | |
| 2014/0081253 A1 | 3/2014 | Kumar et al. | | |
| 2015/0150459 A1 * | 6/2015 | Werahera | ............ | A61B 8/0841 600/411 |
| 2016/0008074 A1 * | 1/2016 | Glossop | ............ | A61B 17/0218 606/130 |
| 2016/0310215 A1 * | 10/2016 | Palma | ............ | A61B 34/10 |
| 2016/0338679 A1 * | 11/2016 | Tehrani | ............ | A61B 5/0035 |
| 2017/0014641 A1 * | 1/2017 | Leong | ............ | A61N 5/1027 |
| 2017/0020558 A1 * | 1/2017 | Xu | ............ | A61B 8/5246 |
| 2017/0020623 A1 * | 1/2017 | Glossop | ............ | A61B 34/10 |
| 2017/0203128 A1 * | 7/2017 | Kung | ............ | A61N 5/1027 |
| 2017/0231602 A1 * | 8/2017 | Venkataraman | ....... | A61B 8/085 600/431 |
| 2017/0301088 A1 * | 10/2017 | Bharat | ............ | A61B 5/4381 |

OTHER PUBLICATIONS

PCT Application No. PCT/US 18/31800, International Search Report and Search History, dated Sep. 26, 2018, 15 pages.

* cited by examiner

CUSTOMIZABLE SATURATION BIOPSY

CROSS REFERENCE TO RELATED APPLICATIONS

This application claims priority under 35 U.S.C. § 119 to U.S. Provisional Patent Application No. 62/504,202, filed on May 10, 2017, hereby incorporated herein by reference in its entirety.

Also, this application relates to and incorporates herein by reference in its entirety U.S. Provisional Patent Application No. 60/700,213, filed on Jul. 18, 2005.

BACKGROUND OF THE INVENTION

1. Field of the Invention

The present invention relates generally to a system and a method, such as described herein, that relates to medical biopsy techniques and devices, and more particularly, to software, software components and systems that facilitate obtaining and presenting biopsy information.

2. Description of Related Art

The American Cancer Society estimates that approximately 220,000 new cases of prostate cancer are diagnosed every year, with 30,000 fatalities directly attributable to the disease. Methods for diagnosing the disease include digital rectal examinations (DREs) as well as blood tests for levels of the Prostate Specific Antigen (PSA). A positive DRE and rising PSAs are indicative of the presence of prostate cancer and are used to prescribe core biopsies. These biopsies are largely performed trans-rectally under ultrasound guidance.

Disadvantages of the trans-rectal biopsy technique include a relatively high false positive rate, a lack of positional accuracy, and a low repeatability of results and sampling positions. Researchers have suggested the use of a template-guided transperineal approach, termed saturation biopsy, in an effort to overcome these disadvantages.

The saturation biopsy technique involves obtaining multiple tissue core samples from multiple regions of the prostate gland or other biopsy site. For example, the prostate gland is divided into eight sub-regions depending on their location (cephalad-caudal, left-tight, or superior-inferior) within the gland. Core biopsy samples are then obtained under ultrasound guidance from each of the eight sub-regions within the gland. These tissue samples are put into vials and sent to a pathology laboratory for histopathologic testing. The laboratory sends back to the clinician a report indicating which of the vials are detected to have cancerous cells. This information can then be used by the clinician to selectively treat regions of the gland or a lesion site known to have cancer, such as by direct focal treatments including modalities of heat, cold, radiation, and chemical or biological agents.

Accordingly, it can be desirable to facilitate the effective acquisition and use of information in saturation biopsy techniques for diagnosing, managing and treating cancer and other diseases.

SUMMARY OF THE INVENTION

Embodiments of methods and apparatuses for customizable saturation biopsy include, according to the present system, an apparatus for customized saturation biopsy having a pathology mapping unit to identify a plurality of regions of a biopsy area. A grid assembly is coupled to the pathology mapping unit, wherein the grid assembly includes a grid disposed externally to the biopsy area. A display is coupled to the pathology mapping unit that displays information corresponding to the plurality of regions of the biopsy area, wherein the pathology mapping unit controls a configuration of the grid and the information corresponding to the plurality of regions of the biopsy area. An image probe can be provided that is coupled to the pathology mapping unit and that acquires at least one image of the biopsy area, and the display can display the at least one image. An interface can be provided that is coupled to the display and that supplies information to the pathology mapping unit. The interface can include at least two visual displays corresponding to the plurality of regions of the biopsy area. The biopsy area can be at least one of a gland, an organ, and a lesion. The grid can be a controllable electromagnetic grid or a visually projected grid. The information corresponding to the plurality of regions can include grid location information, depth of needle insertion and analyzed information of a disease. The pathology mapping unit can automatically determine a schema for identifying the plurality of regions of the biopsy area.

Embodiments of methods and apparatuses for customizable saturation biopsy further include, according to the present system, a computer program product for customizing saturation biopsy procedures having machine executable code that identifies a plurality of regions of a biopsy area. The computer program product includes machine executable code that configures a grid assembly disposed externally to the biopsy area and machine executable code that displays information corresponding to a plurality of regions of the biopsy area and the grid assembly. The computer program product can also include machine executable code that acquires at least one image of the biopsy area and displays the at least one image and machine executable code can also be included for an interface that supplies information to the pathology mapping unit. The interface can include at least two visual displays corresponding to the plurality of regions of the biopsy area. The biopsy area can be at least one of a gland, an organ, and a lesion. The grid assembly can include a controllable physical grid or a visually projected grid. The information corresponding to the plurality of regions can include grid location information, depth of needle insertion and analyzed information of a disease.

Embodiments of methods and apparatuses for customizable saturation biopsy further include, according to the present system, a customizable saturation biopsy system to perform a biopsy, the system including a controller in communication with a pathology mapping unit and a display, the controller being adapted to identify in communication with the pathology mapping unit a plurality of regions of a biopsy area for the biopsy, to configure a grid assembly coupled to the pathology mapping unit disposed externally to the biopsy area to identify or mark one or more sample locations for the biopsy, and to display information on the display corresponding to the plurality of regions of the biopsy area and the grid assembly for the biopsy.

Embodiments of methods and apparatuses for customizable saturation biopsy further include, according to the present system, a method for customizing saturation biopsy having steps for identifying a plurality of regions of a biopsy area and automatically configuring a grid assembly disposed externally to the biopsy area. Information corresponding to the plurality of regions of the biopsy area and the grid assembly is displayed. One or more of the plurality of regions of the biopsy area are each biopsied according to the grid assembly and the information corresponding to the plurality of regions. The grid assembly can include a controllable electromagnetic grid or a visually projected grid. The information corresponding to the plurality of regions can include grid location information, depth of needle insertion, and analyzed information corresponding to a disease.

These and other features of the present invention will become readily apparent upon further review of the following specification and drawings.

DESCRIPTION OF THE DRAWINGS

Unless otherwise indicated, similar reference characters denote corresponding features consistently throughout the attached drawings.

DETAILED DESCRIPTION

Referring now to the figures of the drawings, the figures comprise a part of this specification and illustrate exemplary embodiments of the described system, apparatuses and methods for customizable saturation biopsy, according to the present invention. It is to be understood that in some instances various aspects of the embodiments can be shown schematically or in a way to better facilitate an understanding of aspects of the system, apparatus and methods for customizable saturation biopsy system herein described, and should not be construed in a limiting sense.

Figure 1:
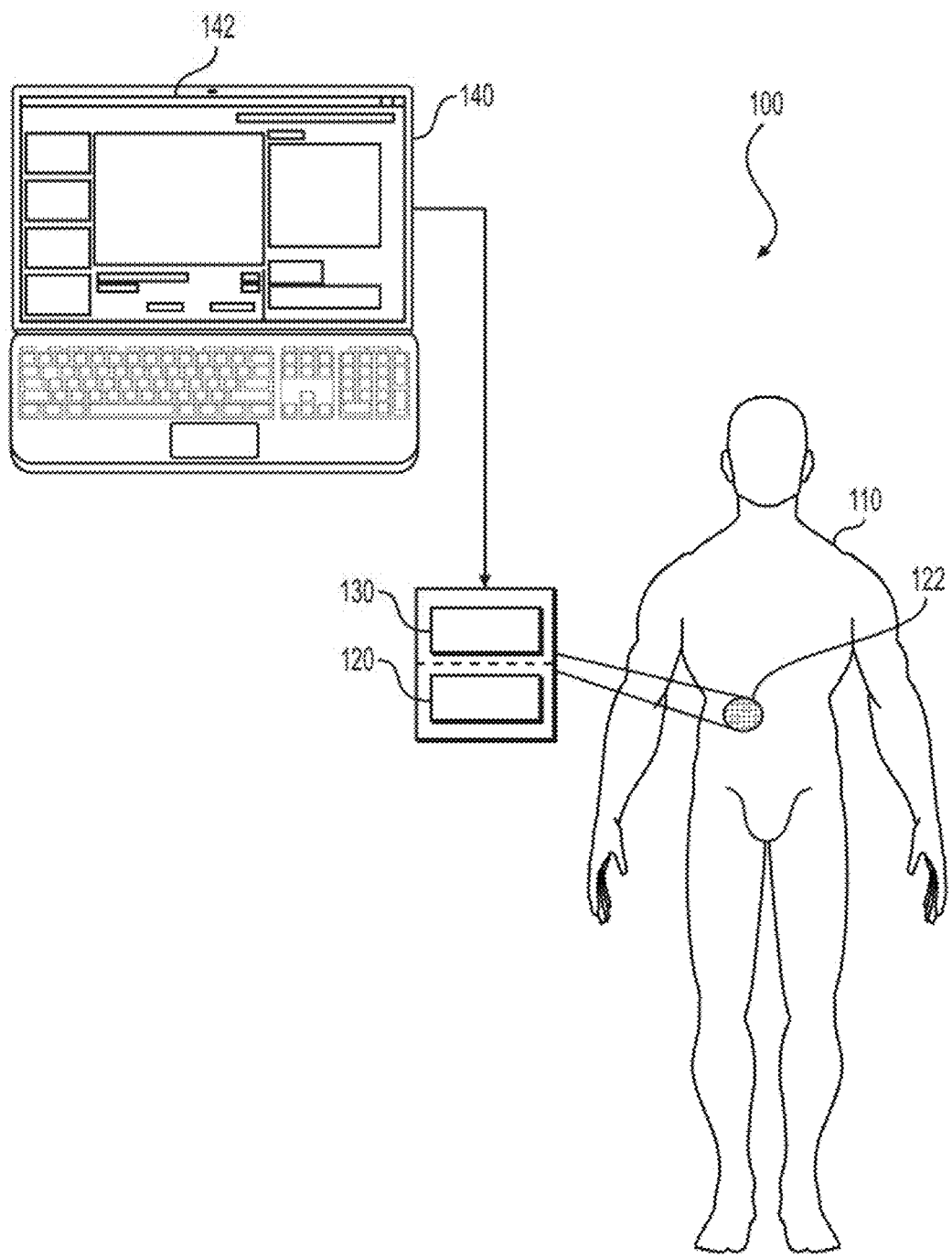
FIG. 1 is a schematic illustration of an embodiment of an apparatus for customizable saturation biopsy, according to the system described herein, according to the present invention.

FIG. 1 is a schematic illustration of customizable saturation biopsy according to the system described herein. The system can be used for mapping the pathology, by region, within any gland or organ, or lesion thereof, within a patient, for example, the liver, gall bladder, kidney and/or others areas and specifically including transperineal biopsies of the prostate. Further, the system can be used in human and veterinary applications. FIG. 1 shows a system 100 to perform saturation biopsy of gland or organ of a human patient 110, for example a lesion in the area of the liver or gall bladder. A grid assembly and fixation system 120 can be used to create a sub-regional biopsy/tissue sampling schema for a biopsy site of the gland or organ. Further, the grid assembly and fixation system 120 can have an area to facilitate attachment of an imaging probe 130 (such as an ultrasound imaging probe or other imaging modality, e.g., nuclear, MRI, CT, x-ray). Alternatively, the imaging probe 130 can be a stand-alone unit from the grid assembly and fixation system 120.

The grid assembly and fixation system 120 can include a floating customizable external grid 122. The external grid 122 can be provided with a given shape or shapes and/or a grid pattern or patterns, as can depend on the use or application. In one embodiment, the external grid 122 is a controllable physical electromechanical grid placed over the region of interest of the patient. In another embodiment, the external grid 122 is visually projected over the region of biopsy interest, for example, by lasers or other suitable visual means, for example.

The image probe or imaging probe 130 images a gland or other region of biopsy interest. Images can be acquired as still images or standard live video, through DICOM or any other imaging standard. Images can be processed online (enhanced) for contrast, sharpness and/or other filtering characteristics. Once the image is created, a pathology mapping unit 140, which is coupled to the imaging probe 130 and/or the grid assembly and fixation system 120, can control information display and the sampling grid pattern of the external grid 122. As further described elsewhere herein, the pathology mapping unit 140 can include software that processes data based on the images (for example, by manual user input or results of automated algorithms) and can include a display 142 that helps guide the clinician on where the next biopsy sample should be taken, for example, with information corresponding to two dimensional (2D) or three dimensional (3D) images, description of grid location and depth of needle insertion. Customizable grids can be created for various applications based on a lesion, gland or organ geometry observed in the images and can be based on probabilistic theory to maximize potential for finding lesions/cancer. Biopsy needles are introduced through the customizable external grid 122, in a planned manner according to the pathology mapping unit 140, to create sub-regional pathology maps for the region of interest, for example. The grid pattern of the external grid 122 can be customized and configured by selective indicators, such as active apertures (electromechanical) that selectively close, open or indicate select areas of the external grid 122 for a subsequent biopsy needle insertion for the biopsy, or utilize visual indicators, such as selective illumination of grid areas with light or a light pattern. The light or lighting can be a predetermined pattern of intensity, luminosity and/or color, such as can vary from constant illumination to selective on/off states of the light to indicate biopsy needle insertion for the biopsy procedure.

The pathology mapping unit 140 can operate as part of a computer, such as a laptop computer or personal digital assistant (PDA) that provides enhanced mobility of the system, with the display 142 being the computer screen. In an embodiment herein, the system operates with a computer running a Windows operating system, for example, or other suitable operating system. The display 142 can include a graphical user interface (GUI), or other suitable interface or display, to help clinicians input, interpret and/or use the pathology data.

Figure 2:
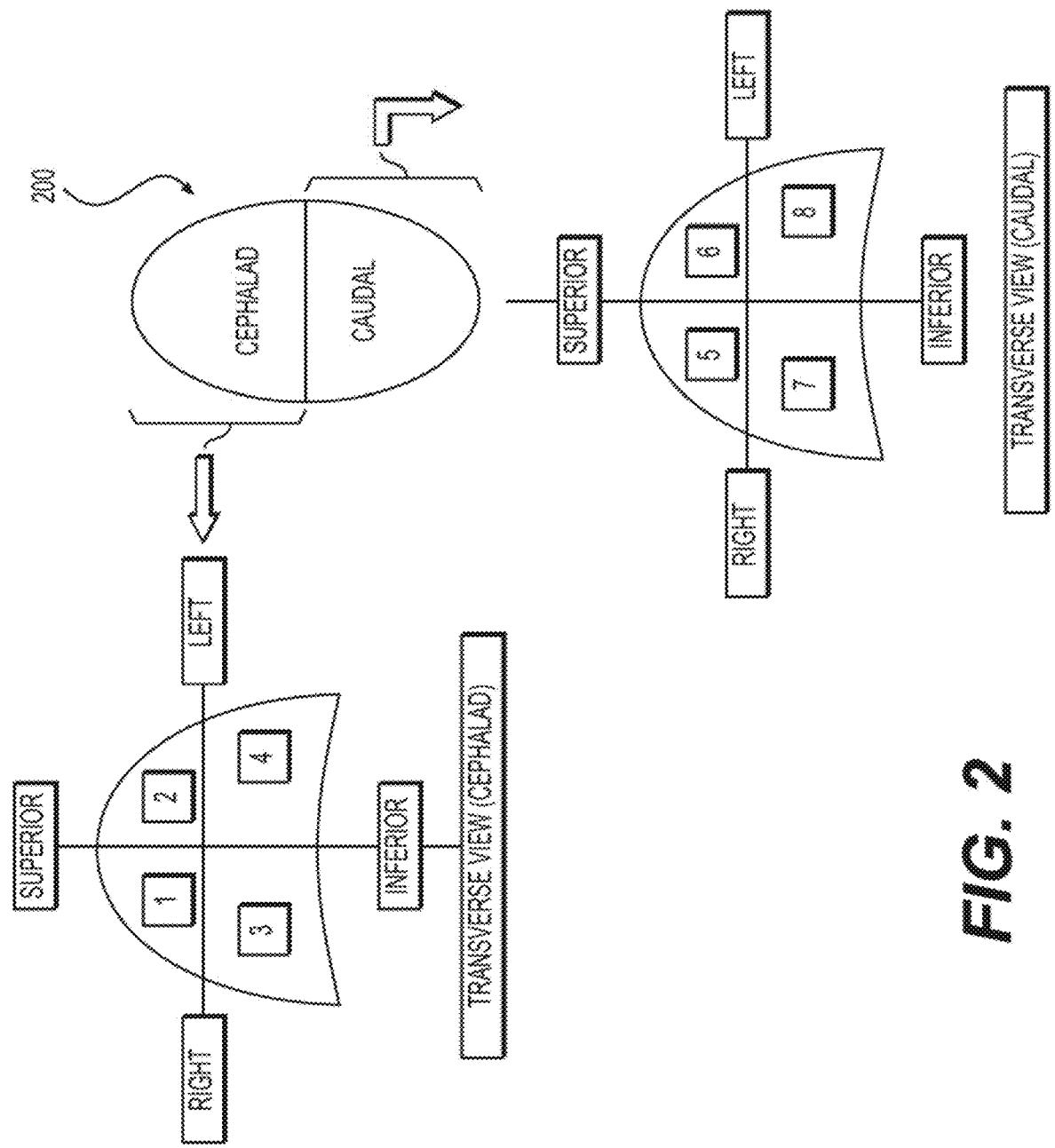
FIG. 2 is a schematic exemplary illustration, such as of a gland 200, that is split into eight sub-regions for saturation biopsy in embodiments of methods and apparatus for customizable saturation biopsy, according to the present invention.

FIG. 2 is a schematic illustration of a gland 200 that is split into eight sub-regions (cephalad-caudal, left-right and superior-inferior) for saturation biopsy according to the system described herein. Other numbers and configurations of sub-regions are possible and contemplated herein. The number and configuration can be based on the application and, generally, the larger the number of sub-regions the more detailed can be the regional map of the area of biopsy interest. Biopsy needles are introduced into one or more of the regions according to the devices and techniques of the system described herein. The biopsy samples are then analyzed for disease, for example by sending to a laboratory for analysis. The data corresponding to whether cancer or other disease exists in the biopsied lesion can be input into the pathology mapping unit. The data can be input manually by a user. Alternatively, the data can be input electronically through a Pathology Information System (IS) or through a tie-in with a Hospital Information System (IDS) (HL-7 or other standard). Data can include yes/no indications of the presence of cancerous, cells, a count of the cells or some other indication of severity, a percentage indication of the likelihood of cancer, or some other indicator or combination of indicators as well as clinician comments and general observations.

In an embodiment herein, the GUI includes a dual template grid display that can match image displays provided by the image probe, such as an ultrasound machine. A portion of the display can be designated for inputting and displaying octant (or other measure) data pertinent to the cephalad octants (1-4), while another part of the display 142 can be used similarly for the caudal octants (5-8). In another embodiment, each of the template display portions can display contours relevant to their octant domains. Thus, for example, the caudal template display portion can only show prostate contours in the caudal part of the gland and vice versa for the cephalad template display.

Figure 3:
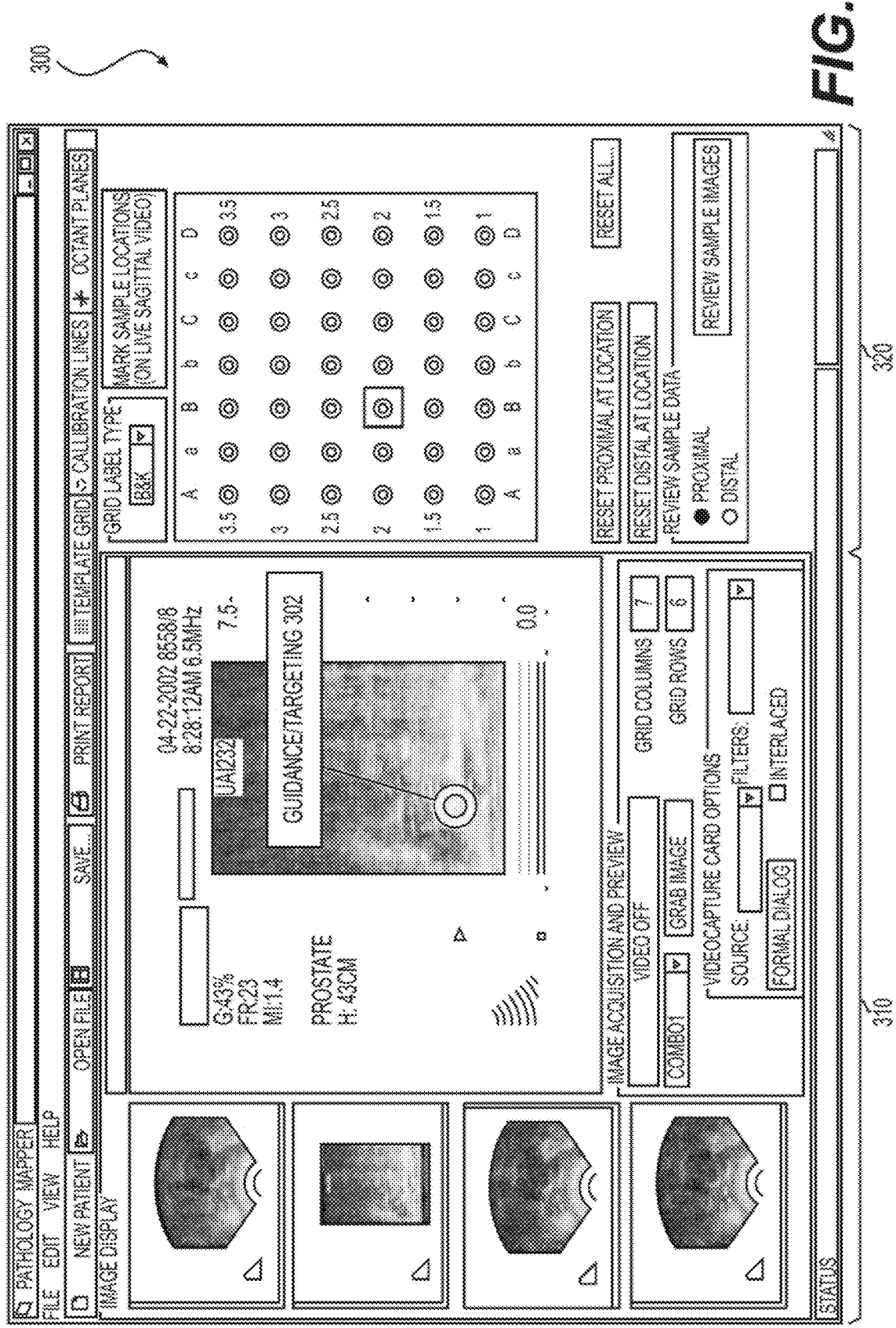
FIG. 3 is an exemplary screen display illustrating a graphic user interface (GUI) of a pathology mapping unit according to the system described herein, in embodiments of methods and apparatus for customizable saturation biopsy, according to the present invention.

FIG. 3 is a screen display illustration of a GUI 300 of a pathology mapping unit according to the system described herein. The GUI 300 shows saturation biopsy data for saturation biopsy of a prostate. One display portion of the GUI 300 includes image information 310 and another portion includes biopsy grid information 320 for generating and displaying the customized grid pattern for the external grid 122 for the biopsy procedure. The image information 310 can include both still images and video images of an area to be biopsied. A clinician can interact with the GUI 300 to modify the biopsy grid information 320 that generates the schema for the customized grid pattern for the external grid 122 for performing a biopsy at a site. The biopsy grid information can include the customized grid or light patterns for the eternal grid 122, as described.

The system described herein can include at least two modes of operation. One operational mode is the "tissue sample acquisition" mode, in which the system provides targeting data corresponding to where and at what depth to take a biopsy sample. Another operational mode is the "pathology data review" mode in which the image is overlaid with information regarding the pathology found at the biopsied regions (for example, cancer (yes/no), Gleason grade, nature, and/or other information). Both the image information 310 and the biopsy grid information 320 of the GUI 300 can be utilized to help the clinician in the saturation biopsy process in each of the above-described operational modes.

As noted herein, the system can allow the clinician to interact with the GUI 300, for example by use of an input device, such as a mouse. The clinician can target the site of an area around which to create a biopsy schema by clicking on the appropriate location, for example in either cephalad or caudal template displays as a reference using a template hole or aperture location. Based on the location of the clinician's click, the system, using a software module described elsewhere herein, automatically determines the octant, or other region measure, of the area for biopsy using a stored algorithm. Furthermore, once information regarding the patient's anatomy, biopsy location data, and pathology data is acquired, the data can be saved and then electronically transmitted (for example, via proprietary data format files, DICOM-RT or other standards) for use in treatment planning and/or for more ensuring biopsies.

The pathology mapping unit 140 (see, FIG. 1) can include a saturation biopsy software module (SBSM) having machine executable code that provides customizable control of various aspects of the saturation biopsy process. The SBSM allows clinicians to acquire images from an ultrasound machine or other imaging source and identify the anatomical target as well as surrounding anatomy to biopsy. Further, as described elsewhere herein, the system can allow the clinician to interact with a graphical user interface (GUI), for example with a mouse, to identify a biopsy site of interest and develop a biopsy schema or plan for the site. The SBSM can also generate two dimensional (2D) and/or three dimensional (3D) graphics illustrating the locations of the site.

Figure 4:
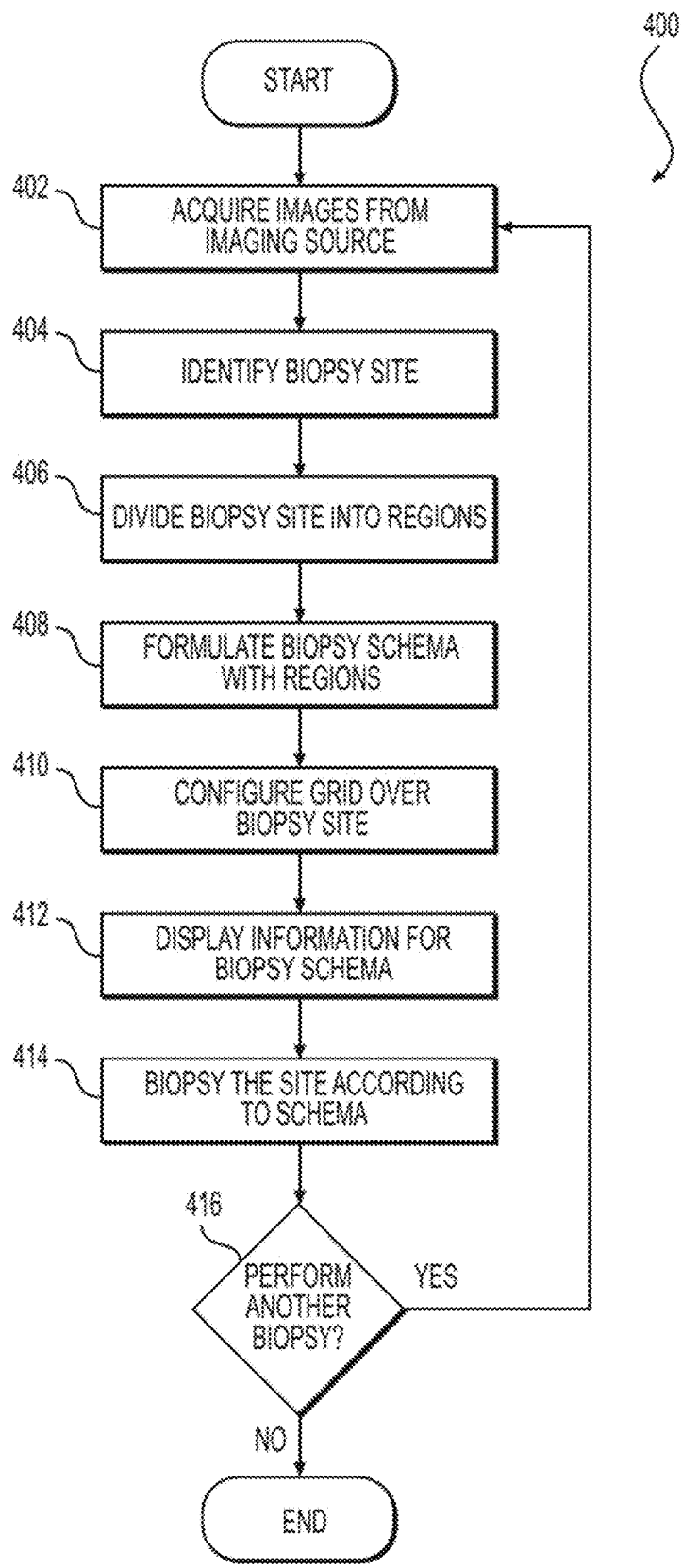
FIG. 4 is a schematic flow diagram of a tissue sample operational mode of an embodiment of a saturation biopsy process, according to the system described herein, in embodiments of methods and apparatus for customizable saturation biopsy, according to the present invention.

FIG. 4 is a schematic flow diagram 400 of a tissue sample operational mode of a saturation biopsy process according to the system described herein. At step 402, images of a region of interest are acquired using an imaging system, such as an ultrasound imaging system. At step 404, a site for biopsy is identified, for example by a clinician interfacing with the system using a GUI, as further described elsewhere herein. At step 406, the system divides the biopsy site into regions, for example into octants. At step 408, the system formulates a saturation biopsy schema based on the divided regions. At step 410, the system configures a grid externally over the biopsy site on the patient's body. As further described elsewhere herein, the grid can be a physical grid that is controllable by the present system and can also be a visual grid produced, for example, by lasers. At step 412, the system displays information to a clinician corresponding to the biopsy schema. Information displayed can include grid locations and depths of needle insertion for the biopsy procedure. At step 414, the clinician oversees biopsies at the biopsy site according to the schema as guided by the grid and the display information of the system. At decision step 416, if another biopsy is to be performed, processing proceeds back to step 402. The above steps can be implemented by machine executable code stored in a computer readable storage medium.

Figure 5:
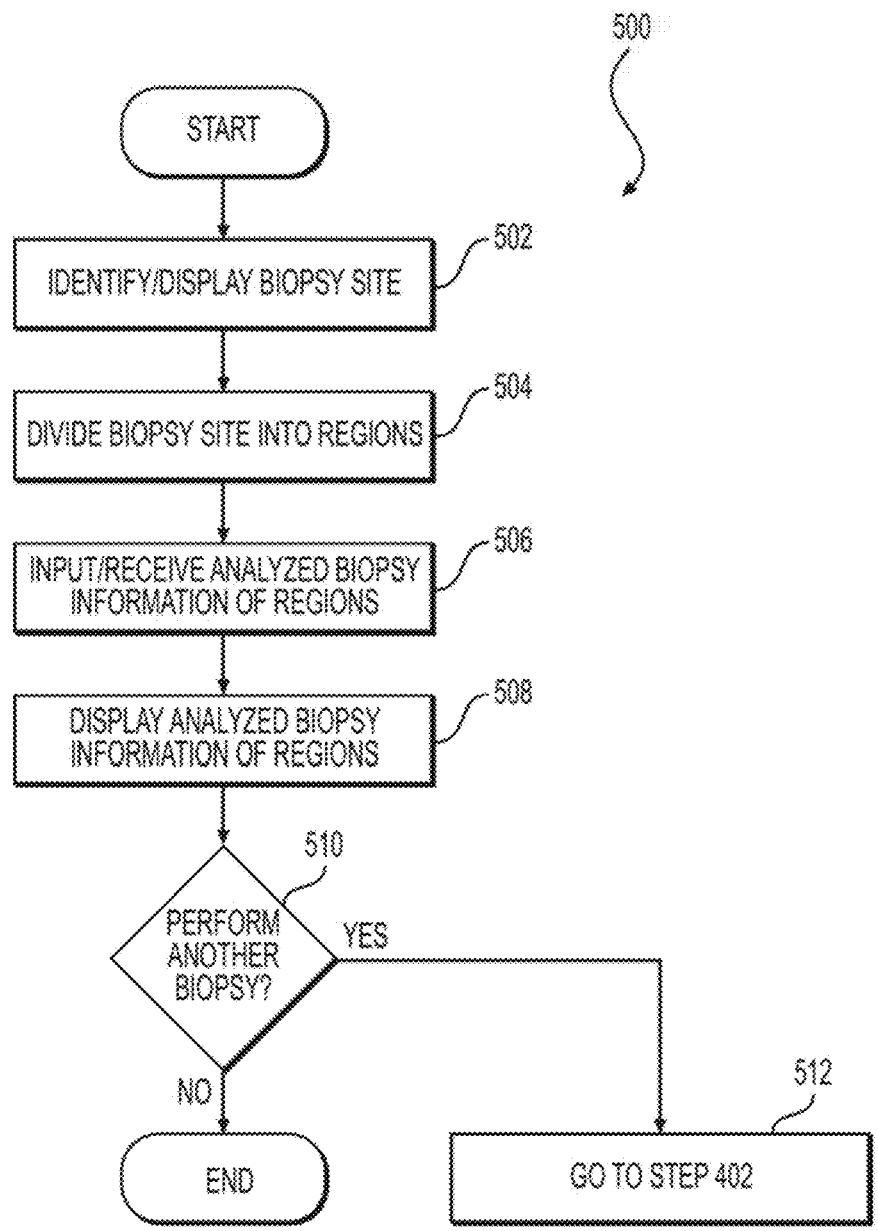
FIG. 5 is a schematic flow diagram of an embodiment of a pathology review operational mode of an embodiment of a saturation biopsy process, according to the system described herein, in embodiments of methods and apparatus for customizable saturation biopsy, according to the present invention.

FIG. 5 is a schematic flow diagram 500 of a pathology review operational mode of a saturation biopsy process according to the system described herein. At step 502, a biopsy site is identified and images are displayed. Images displayed can include images previously taken when the tissue sampling procedure was performed or can include new images. At step 504, the biopsy site is divided into regions consistent with the regions identified during the tissue sampling procedure. At step 506, analyzed biopsy information is received by the system. The analyzed biopsy information can be manually input by the clinician viewing a lab report of the biopsied samples or the information can be electronically transmitted from the lab via a pathology information system or other medical information system. At step 508, the analyzed biopsy information is displayed. For example, the analyzed biopsy information can be displayed as an overlay in conjunction with images of the biopsy site.

At decision step 510, following review and an analysis by the clinician, the clinician decides whether further saturation biopsy procedures are appropriate. If so, then step 512 indicates that processing returns to step 402 of the tissue sampling mode flow diagram. The above steps can be implemented by machine executable code stored in a computer readable storage medium. The information and data provided by the system described herein can then be used to develop conformal treatment plans to help eradicate the cancer or other disease.

Figure 6:
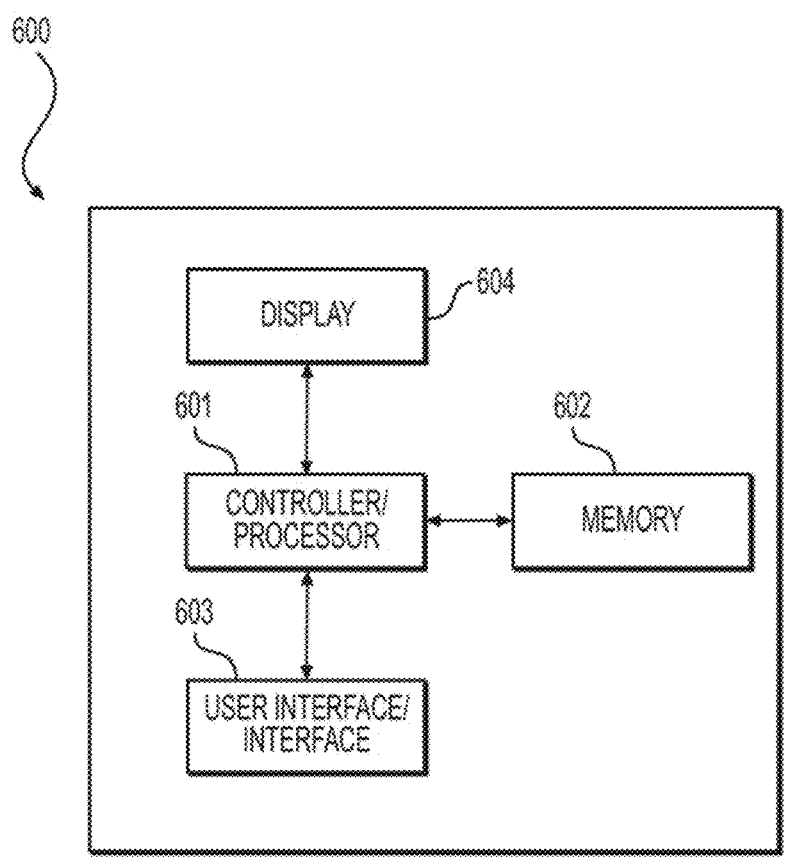
FIG. 6 is a block diagram of an exemplary main controller or control system, according to the system described herein, in embodiments of methods and apparatus for customizable saturation biopsy, according to the present invention.

Referring to FIG. 6, there is illustrated therein a generalized main controller or control system 600 for use in embodiments of methods and apparatuses for customizable saturation biopsy to implement the operations and processes of the pathology mapping unit 140, which is coupled to the imaging probe 130 and/or the grid assembly and the fixation system 120, to control information display and the sampling grid pattern of the external grid 122.

As further described elsewhere herein, a controller/processor 601 of the control system 600 is programmed to implement and control the processes and methods of customizable saturation biopsy of the pathology mapping unit 140 and other components of the described system, as herein described, and to process data based on the images (for example, by manual user input, such as through a user interface/interface 603, or results of automated algorithms implemented by the controller/processor 601).

The controller/processor 601 also controls a display 604 of the control system 600 for display of information, such as the display 142 or the GUI 300, and that can help guide the clinician on where the next biopsy sample should be taken, for example. A memory 602 of the control system 600 can include data and information storage for the saturation biopsy and store the requisite software, programs and/or algorithms for implementation and control of processes and apparatus for the customizable saturation biopsy, such as described herein. The control system 600 can also include the user interface/interface 603 for viewing information and data and inputting information or control instructions for the processes and methods of the customizable saturation biopsy.

The control system 600 can represent, for example, a stand-alone computer, computer terminal, portable computing device, networked computer or computer terminal, or networked portable device. Data or control instructions can be entered into the control system 600 by the user via any suitable type of user interface as the user interface/interface 603, and can be stored in computer readable memory as the memory 602, which can be any suitable type of computer readable and programmable memory. Calculations are performed by the controller/processor 601, and also the processing operations of the various described components of the control system 600, which can be any suitable type of computer processor, and can be displayed to the user on the display 604 of the control system 600, such as the display 142 or the GUI 300, which can be any suitable type of computer display, for example.

Examples of computer readable media include a magnetic recording apparatus, non-transitory computer readable storage memory, an optical disk, a magneto-optical disk, and/or a semiconductor memory (for example, RAM, ROM, etc.). Examples of magnetic recording apparatus that can be used in addition to memory 602, or in place of memory 602, include a hard disk device (HDD), a flexible disk (FD), and a magnetic tape (MT). Examples of the optical disk include a DVD (Digital Versatile Disc), a DVD-RAM, a CD-ROM (Compact Disc-Read Only Memory), and a CD-R (Recordable)/RW.

Other embodiments of the invention will be apparent to those skilled in the art from a consideration of the specification or practice of the invention disclosed herein. It is intended that the specification and examples be considered as exemplary only, with the scope and spirit of the invention being indicated by the following claims. Also, it is to be understood that the present invention is not limited to the embodiments described above, but encompasses any and all embodiments within the scope of the following claims.

We claim:

1. An apparatus for customized saturation biopsy, comprising:
   a pathology mapping unit for identifying a plurality of regions of a biopsy area to perform a biopsy;
   a grid assembly coupled to the pathology mapping unit, the grid assembly having an external grid, the external grid being one of a floating grid visually and physically projected onto the biopsy area or a controllable electromechanical grid overlying the biopsy area, the electromechanical grid having at least one select aperture actuatable between open and closed states; and
   a display coupled to the pathology mapping unit to display information corresponding to the plurality of regions of the biopsy area for the biopsy,
   wherein the pathology mapping unit is configured to control a configuration of the external grid and the information corresponding to the plurality of regions of the biopsy area for the biopsy without one or more markers in conjunction with the grid assembly.

2. The apparatus of claim 1, further comprising:
   an imaging probe coupled to the pathology mapping unit configured to acquire at least one image of the biopsy area,
   wherein the display is configured to display the at least one image for the biopsy.

3. The apparatus of claim 1, further comprising:
   an interface coupled to the display, the interface being configured to supply information for the biopsy to the pathology mapping unit.

4. The apparatus of claim 3, wherein:
   the interface includes at least two visual displays corresponding to the plurality of regions of the biopsy area.

5. The apparatus of claim 1, wherein:
   the biopsy area is at least one of a gland, an organ or a lesion.

6. The apparatus of claim 1, wherein:
   the controllable electromechanical grid comprises a plurality of apertures including the at least one select aperture, the at least one select aperture of the plurality of apertures being selectively and actively actuatable in an electromechanical manner to open or close the at least one select aperture independently from the remainder of the plurality of apertures for selective access to a select area for the biopsy.

7. The apparatus of claim 1, wherein:
   the information corresponding to the plurality of regions for the biopsy includes at least one of grid location information or a depth of needle insertion for the biopsy.

8. The apparatus of claim 1, wherein:
   the information corresponding to the plurality of regions for the biopsy includes analyzed information of a disease for which to perform the biopsy.

9. The apparatus of claim 1, wherein:
the pathology mapping unit automatically determines a schema to identify the plurality of regions of the biopsy area for the biopsy.

10. A customizable saturation biopsy system to perform a biopsy, the system comprising a controller, a pathology mapping unit and a display, the controller being adapted to:
identify in communication with the pathology mapping unit a plurality of regions of a biopsy area for the biopsy;
configure a grid assembly coupled to the pathology mapping unit disposed externally to the biopsy area to identify one or more sample locations for the biopsy, the grid assembly having an external grid, the external grid being one of a floating grid visually and physically projected onto the biopsy area or a controllable electromechanical grid overlying the biopsy area, the electromechanical grid having at least one select aperture actuatable between open and closed states, the pathology mapping unit identifying one or more sample locations for the biopsy without one or more markers in conjunction with the grid assembly; and
display information on the display corresponding to the plurality of regions of the biopsy area and the grid assembly for the biopsy.

11. The system of claim 10, further comprising:
an imaging probe in communication with the controller, the controller being further adapted to acquire at least one image of the biopsy area from the imaging probe and to display the at least one image on the display.

12. The system of claim 10, further comprising:
an interface in communication with the controller, the controller being further adapted to supply information from the interface to the pathology mapping unit.

13. The system of claim 12, wherein:
the interface includes at least two visual displays corresponding to the plurality of regions of the biopsy area.

14. The system of claim 10, wherein:
the biopsy area is at least one of a gland, an organ or a lesion.

15. The system of claim 10, wherein:
the controllable electromechanical grid comprises a plurality of apertures including the at least one select aperture, the at least one select aperture of the plurality of apertures being selectively and actively actuatable in an electromechanical manner to open or close the at least one select aperture independently from the remainder of the plurality of apertures for selective access to a select area for the biopsy.

16. The system of claim 10, wherein:
the information corresponding to the plurality of regions for the biopsy includes at least one of grid location information or a depth of needle insertion for the biopsy.

17. The system of claim 10, wherein:
the information corresponding to the plurality of regions for the biopsy includes analyzed information corresponding to a disease for which to perform the biopsy.

18. A method for customized saturation biopsy, comprising:
identifying a plurality of regions of a biopsy area for a biopsy;
automatically configuring a grid assembly disposed externally to the biopsy area, the grid assembly having an external grid, the external grid being one of a floating grid visually and physically projected onto the biopsy area or a controllable electromechanical grid overlying the biopsy area, the electromechanical grid having at least one select aperture actuatable between open and closed states, the identifying the plurality of regions of the biopsy area being performed without one or more markers in conjunction with the grid assembly;
displaying information corresponding to the plurality of regions of the biopsy area and the grid assembly; and
performing the biopsy in one or more of the plurality of regions of the biopsy area according to the grid assembly identifying one or more sample locations for the biopsy and the information corresponding to the plurality of regions.

19. The method of claim 18, wherein:
the information corresponding to the plurality of regions includes at least one of grid location information for the one or more sample locations for the biopsy, a depth of needle insertion or analyzed information corresponding to a disease for which to perform the biopsy.

* * * * *